United States Patent [19]
Prekel et al.

[11] Patent Number: 5,841,138
[45] Date of Patent: Nov. 24, 1998

[54] METHOD OF AN APPARATUS FOR NONDESTRUCTUVE WORKPIECE TESTING

[75] Inventors: Helmut Prekel, Lindau; Horst Adams, Nonnenhorn, both of Germany

[73] Assignee: Wagner International AG, Altstatten, Switzerland

[21] Appl. No.: 763,245

[22] Filed: Dec. 10, 1996

[30] Foreign Application Priority Data

Dec. 21, 1995 [DE] Germany ................ 195 48 036.8

[51] Int. Cl.$^6$ .................................................. G01N 15/08
[52] U.S. Cl. ................ 250/341.1; 250/347; 250/358.1; 356/381
[58] Field of Search ................ 250/341.8, 341.1, 250/347, 358.1; 356/381, 369

[56] References Cited

U.S. PATENT DOCUMENTS 3,569,696  3/1971  Karlson ................ 250/341.1

FOREIGN PATENT DOCUMENTS

| 0 609 193 A2 | 8/1994 | European Pat. Off. | ........ G01N 15/08 |
| 25 21 037 | 11/1975 | Germany | ........ G01B 11/30 |
| 0228916 | 10/1985 | Germany | ........ 250/341.8 |
| 36 31 652 A1 | 3/1988 | Germany | ........ G01B 15/02 |
| 42 23 337 C2 | 1/1994 | Germany | ........ G01N 21/17 |

OTHER PUBLICATIONS

S. O. Kanstad and Per–Erik Nordal, "Experimental aspects of photothermal radiometry", Can. J. Phys., vol. 64, 1986, pp. 1155–1164.

C. A. Bennett, Jr. and R. R. Patty, "Thermal wave interferometry: a potential application of the photoacoustic effect", Applied Optics, vol. 21, No. 1, Jan. 1, 1982, pp. 49–54.

*Primary Examiner*—Edward P. Westin
*Assistant Examiner*—Richard Hanig
*Attorney, Agent, or Firm*—Fenwick & West, LLP

[57] ABSTRACT

A nondestructive workpiece testing method and apparatus are provided, wherein an electromagnetic, intensity modulated excitation beam is directed at a point of examination on a workpiece surface, and wherein thermal radiation emitted by the point of examination is detected and evaluated, the excitation beam being guided periodically in different directions in each one of which it is directed at a different point of examination on a workpiece surface. Moreover, an apparatus is provided for nondestructive workpiece testing, comprising an excitation source for the emission of an electromagnetic excitation beam, an optical means to modulate the intensity of the excitation beam and to direct the excitation beam at a point of examination on a workpiece surface, further comprising a detector means to detect the thermal radiation emitted by the point of examination. The optical means comprises modulating means for periodically deflecting the excitation beam in different directions as well as directional means for directing the excitation beam in each direction at a different point of examination on a workpiece surface.

18 Claims, 3 Drawing Sheets

METHOD OF AN APPARATUS FOR NONDESTRUCTUVE WORKPIECE TESTING

FIELD OF THE INVENTION

The instant invention relates to a nondestructive workpiece testing method, wherein an electromagnetic, intensity modulated excitation beam is directed at a point of examination on a workpiece surface, and wherein thermal radiation emitted by the point of examination is detected and evaluated. The invention also relates to an apparatus for nondestructive workpiece testing, comprising an excitation source for the emission of an electromagnetic excitation beam, an optical means to modulate the intensity of the excitation beam and direct the excitation beam at a point of examination on a workpiece surface, further comprising a detector means to detect the thermal radiation emitted by the point of examination.

BACKGROUND OF THE INVENTION

Nondestructive and contact-free testing of material by means of thermal excitation of surfaces, applying intensity modulated radiation and evaluating the course in time of the heat radiation emitted by the surface, is a process which has proved successful for some years. The underlying principle, also known as photothermal radiometry (PTR), is based on the generation of temperature waves in a specimen to be tested, such waves spreading in a manner which is characteristic of the condition of the material of the specimen and being diffused or reflected at thermal inhomogeneities, such as layer boundaries, delaminations, fissures, pores, etc., in a way similar to ultrasonic waves. Essential differences over ultrasonic methods reside in stronger attenuation and a much lower dispersion speed. The reflected or scattered portions of the temperature wave interfere with the original or excitation wave, forming a sum vector of the temperature wave, in part also upon multiple reflections or dispersions. This sum vector contains a vector quantity and a phase as measurement information about the specimen under investigation, the vector quantity as such being hardly useful because of its great dependence on external factors, such as the measuring distance and irradiation angle, both of which cannot be adjusted with sufficient accuracy in industrial application. The phase, on the other hand, is largely independent of these parameters and even of the power of the intensity modulated excitation radiation so that it can be evaluated reliably. The condition of a workpiece surface, e.g. the thickness can be determined based on the shift in phase of the thermal radiation emitted by the workpiece, as compared to the excitation irradiation.

It is convenient to select the excitation radiation such that its wavelength(s) is/are outside the sensitivity range of the infrared detector. In that event scattered and/or reflected excitation radiation can be prevented from producing a noise signal in the detector.

Photothermal radiometry is especially useful for workpieces which are thermally thin, such as surface coatings and protective layers on workpieces, because then the interferences of the temperature waves manifest themselves most clearly. Further theoretical aspects of photothermal radiometry are discussed by C. A. Bennett, Jr. and R. R. Patty in "Thermal Wave Interferometry: A Potential Application of the Photoacoustic Effect", Applied Optics, vol. 21, no. 1, Jan. 1, 1982, pp. 49 to 54.

An apparatus for nondestructive material testing is known from EP-A-0 609 193. In that case a modulated laser beam or a continuous laser beam modulated (interrupted periodically) by a mechanical interrupter is directed at a test surface so as to cause periodic heating on the same. This then is sensed by an infrared detector, converted, and applied to a computer for evaluation so that the porosity of friction linings may be determined.

Another arrangement for photothermal testing of material or layer thickness measurement is taught by DE-A-36 31 652. FIG. 1 of that publication shows a heat radiator with a downstream modulator by means of which intensity modulated radiation is applied, in this case through a fiber, to the surface to be tested.

The excitation source used in such a system to generate the excitation beam, as a rule, is a costly component, especially so if it is a laser, as in the case of EP-A-0 609 193; apart from the high costs of acquisition and maintenance, usually also the operating costs are high due, among others, to the poor efficiency and high energy consumption of quite some lasers and also to the great expenditure involved in cooling the laser.

In the case of each of the examples mentioned of photothermal testing apparatus, the excitation source which generates the intensity modulated excitation beam is not exploited more than 50%, at best. With the modulated mode of operation of the laser according to EP-A-0 609 193 at least the radiation generated is fully utilized, but not the laser unit itself. On the other hand, 50% of the radiation energy generated remain unused when continuous radiation is modulated by means of an interrupter, as is the case with EP-A-0 609 193 and DE-A-36 31 652. This cutting out of 50% of the radiation energy may lead to thermal problems within the apparatus and perhaps even falsify the signals due to "vagabonding" infrared radiation.

It is necessary or at least desirable in many industrial applications that a number of different locations on the surface of a workpiece be examined at the same time. A typical coating installation, for example, consists of a conveyor system for moving workpieces through a coating compartment in which varnish is applied either to two sides of one workpiece each or to one side each of two workpieces being conveyed in pairs. As both sides of the coating equipment normally do not operate exactly alike, i.e. do not automatically provide the same layer thicknesses at the same operating parameters, it is necessary for quality assurance purposes to monitor both sides of the coating by means of some measuring technique.

When applying measuring systems, such as those specified in EP-A-0 609 193 or DE-A-36 31 652, each measuring station needs a complete measuring or testing system, each with its own excitation source. No apparatus has become known so far which would permit a plurality of points on a workpiece under examination to be analyzed simultaneously by means of a single excitation source.

SUMMARY OF THE INVENTION

It is, therefore, an object of the instant invention to indicate a method and an apparatus by which workpieces can be tested in nondestructive fashion, examining a plurality of points of a workpiece at the same time. It is another object of the invention to suggest a method and an apparatus of the kind in question to be available at a lower purchasing price and reduced operating cost, compared to the known methods and apparatus.

The above objects are met by a method and by an apparatus according to the invention that permit simultaneous examination of a plurality of points of one or more workpieces by 100% utilization of the radiating power of a single excitation source. In a coating installation, for instance, the method and apparatus according to the invention thus make it possible to measure the layer thickness at both sides being coated.

With the method and apparatus provided by the invention, an excitation source continuously emits an excitation beam which is switched periodically by a suitable structural component between at least two directions or angular positions (channels). In this manner 100% of the radiating power of the excitation source is utilized and either one of the channels is switched on alternately. If two angular positions and thus two channels are provided the resulting duty cycle is 50% of the modulated excitation radiation. The excitation beams of the two channels are shifted in phase by 180° with respect to each other. The power of radiation thus modulated of the two channels, therefore, is available for thermal excitation of at least two different points of examination, e.g. at different sides of a workpiece in a coating installation. The points of examination on the workpiece surface periodically heat up as the excitation beam hits them. The temperature behavior in time of the points under examination, which is characteristic of the surface condition, such as layer thickness, adherence of the layer and composition, is detected individually by radiometry for each point measured and then evaluated by suitable electronic means and software. The phase shift of the excitation on radiation by 180° may be taken into account without any problem in the signal evaluation. Each excitation beam in turn may be split, e.g. by a beam splitter into two or more component beams so as to increase the number of points available for measurement and evaluation.

A related arrangement of the kind in question is described in "Experimental aspects of photothermal radiometry" by S. O. Kanstad, CAN. J. PHYS., vol. 64, 1986, pp. 1155 to 1164. It makes use of a metallized chopper wheel to modulate the excitation radiation and decouple 50% of the radiation to apply it to a power meter because, with this embodiment, the measuring system must be standardized in respect of laser power. However, as mentioned initially, it is preferably the phase of the induced temperature oscillation which is utilized in photothermal surface examination so that, as a rule, it is not necessary to measure the power. Consequently, the corresponding part of the excitation radiation is available for use in exciting another point of examination.

BRIEF DESCRIPTION OF THE DRAWING

The invention will be described further, by way of example, with reference to the accompanying drawings, in which.

DESCRIPTION OF THE PREFERRED EMBODIMENTS

Figure 1:
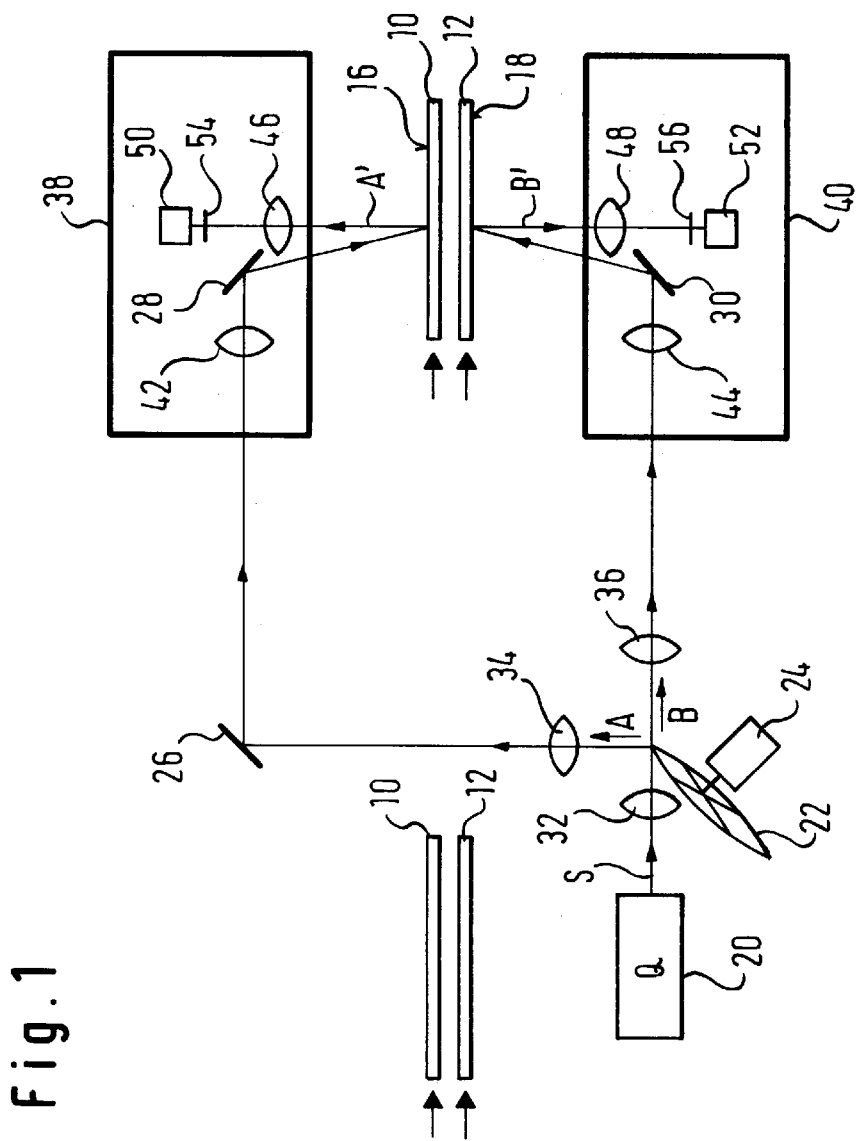
FIG. 1 is a diagrammatic presentation of a first embodiment of the invention.
Figure 1:
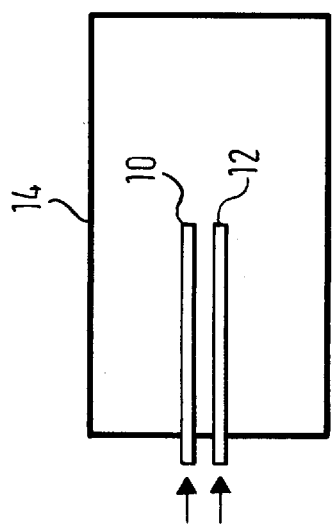

The same reference numerals are used in the three figures to designate like components which will be described only once.

FIG. 1 is a diagrammatic presentation of a first embodiment of the invention. At the left hand side in FIG. 1 two workpieces 10 and 12 may be seen side by side. They are introduced into a coating compartment, indicated merely diagrammatically as a box 14. In the coating compartment, two outer surfaces 16 and 18 of the workpieces 10 and 12 are coated and subjected, either simultaneously or subsequently, to a surface examination, such as measurement of the coating layer thickness or checking of the surface roughness.

An excitation source 20 generates electromagnetic excitation radiation S. It is assumed with this embodiment that the excitation source 20 is a laser source which emits a laser beam S. However, it is likewise possible to use infrared light or electromagnetic radiation having a different wavelength. A rotatable mirror 22 having an axis of rotation perpendicular to the plane of the mirror is disposed in the exit path of the laser beam S.

At its periphery, the mirror 22 is formed with recesses or cuts, and it is either rotated continually or moved back and forth in oscillating motions between two defined angular positions. The excitation beam S hitting the mirror surface is transmitted, if it happens to meet a recess, or it is deflected by reflection, all depending on the position of the mirror. In a preferred embodiment the mirror is round and segments are cut out of its circumference at regular intervals.

The rotatable mirror axis, for example, may the axis of a motor, a scanner, or a rotary magnet or it may be a separate axis of rotation driven by either one of the means mentioned.

The rotational or reciprocating movement of the mirror 22 modulates the continuous excitation beam S at a duty cycle of approximately 50%, thereby providing two excitation beams A and B which are shifted in phase by approximately 180°. The modulated excitation beams A and B also may be regarded as measuring channels A and B. It is convenient to have the excitation beam S impinge on the mirror surface as far away from the mirror axis as possible and to shape or focus the beam cross section as small as possible in the region of the mirror surface by disposing a lens 32 in front of the mirror 22 as this will result in an approximately rectangular course in time of the intensity modulated excitation radiation for both channels A and B. In this manner all the workpiece surface area elements or points of examination covered by the excitation radiation will receive similar thermal excitation (i.e. at the same duty cycle and the same phase). The influence of any irregularities of the mirror geometry, e.g. the segment cutouts, is smallest if the excitation beam is directed to the mirror at a distance from the mirror axis.

In the arrangement the mirror 22 is followed by other lenses 34 (in channel A) and 36 (in channel B) which serve to collimate and, if desired, widen the beam, together with lens 32, so as to guide it through greater distances. A mirror 26 serves for beam guidance. Additional optical elements, like mirrors will be needed for beam guidance in specific cases of application and according to the particular requirements of a case.

The modulating frequencies to be achieved depend on the number of cutouts or segments formed in the mirror 22 and on the speed of rotation of the drive means used for the mirror. A motor having excellent synchronism will be able to provide modulating frequencies from less than one Hertz to a few hundred Hz.

The excitation beams of both channels A and B finally will be applied to a measuring head 38 and 40, respectively. Each measuring head shapes the excitation beam received, A or B, by refractive and/or reflective optical elements, mirrors 28 and 30 as well as lenses 42 and 44 and directs it to the testing surface 16 or 18 of the workpieces 10 and 12, respectively. The heat radiation A' and B' emitted by the points of examination is infrared radiation which depends on the surface temperature and is applied through imaging optics 46 and 48, respectively, to a corresponding detector 50 or 52. In the embodiments shown the imaging optics are embodied by lenses, but they also might be concave mirrors, for instance. In front of each detector 50 and 52 a filter member 54 and 56, respectively, may be provided, such as a cutoff or edge filter to block the entry of any undesired radiation, for example, radiation modulated at 50, 60 or 100 Hz in the near infrared range originating from plant illumination. The heat radiation sensed by the detectors is processed by downstream electronic and evaluating equipment (not shown) so as to determine, for instance, the layer thickness of a surface coat.

Figure 2:
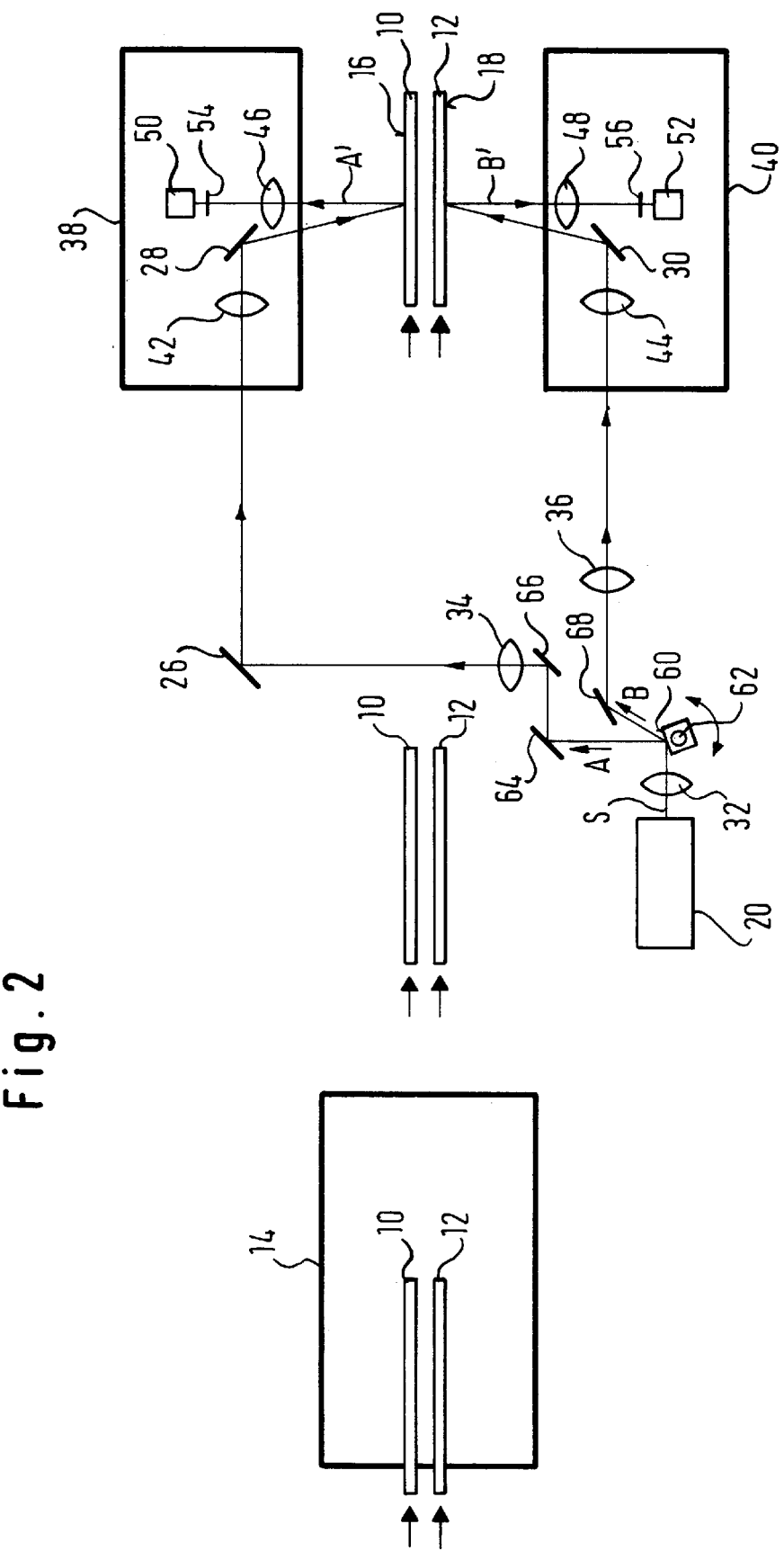
FIG. 2 is a diagrammatic presentation of a second embodiment of the invention.

FIG. 2 illustrates another embodiment of the testing apparatus according to the invention. In FIG. 2 the rotatable mirror of FIG. 1 used to modulate the excitation radiation is substituted by a pivotable mirror 60. The non-segmented mirror 60 is mounted on an axis 62 extending parallel to the plane of the mirror, being adapted to oscillate, and being connected to a drive unit, such as that of a scanner or rotary magnet. The mechanical axis 62 of the pivotable mirror 60 preferably extends through the center of gravity of the mirror so as to avoid any imbalances.

In operation, the mirror 60 hit by excitation radiation S is moved back and forth between two defined angular positions, the excitation beam being deflected between two directions subtending an angle which is twice as great as the angular difference between the two tilted positions of the mirror. The resulting two intensity modulated excitation beams A and B are applied periodically to two measuring heads 38 and 40, as described above with reference to FIG. 1. The modulation frequencies obtainable with this embodiment are greater than approximately 25 Hertz because the mechanical inertia of the oscillation system does not allow the same free adjustment of the duty cycle as does the embodiment shown in FIG. 1.

It is the task of lens 32 to reduce or focus the excitation beam S on the mirror 60. As a consequence, the mirror 60 can be made small and also the inertia of the mechanical oscillation system becomes smaller. As in the case of the embodiment according to FIG. 1, the lenses 34 and 36 serve for collimation and, if desired, widening of the beam, the mirrors 26, 64, 66, and 68 are beam guidance elements.

Figure 3:
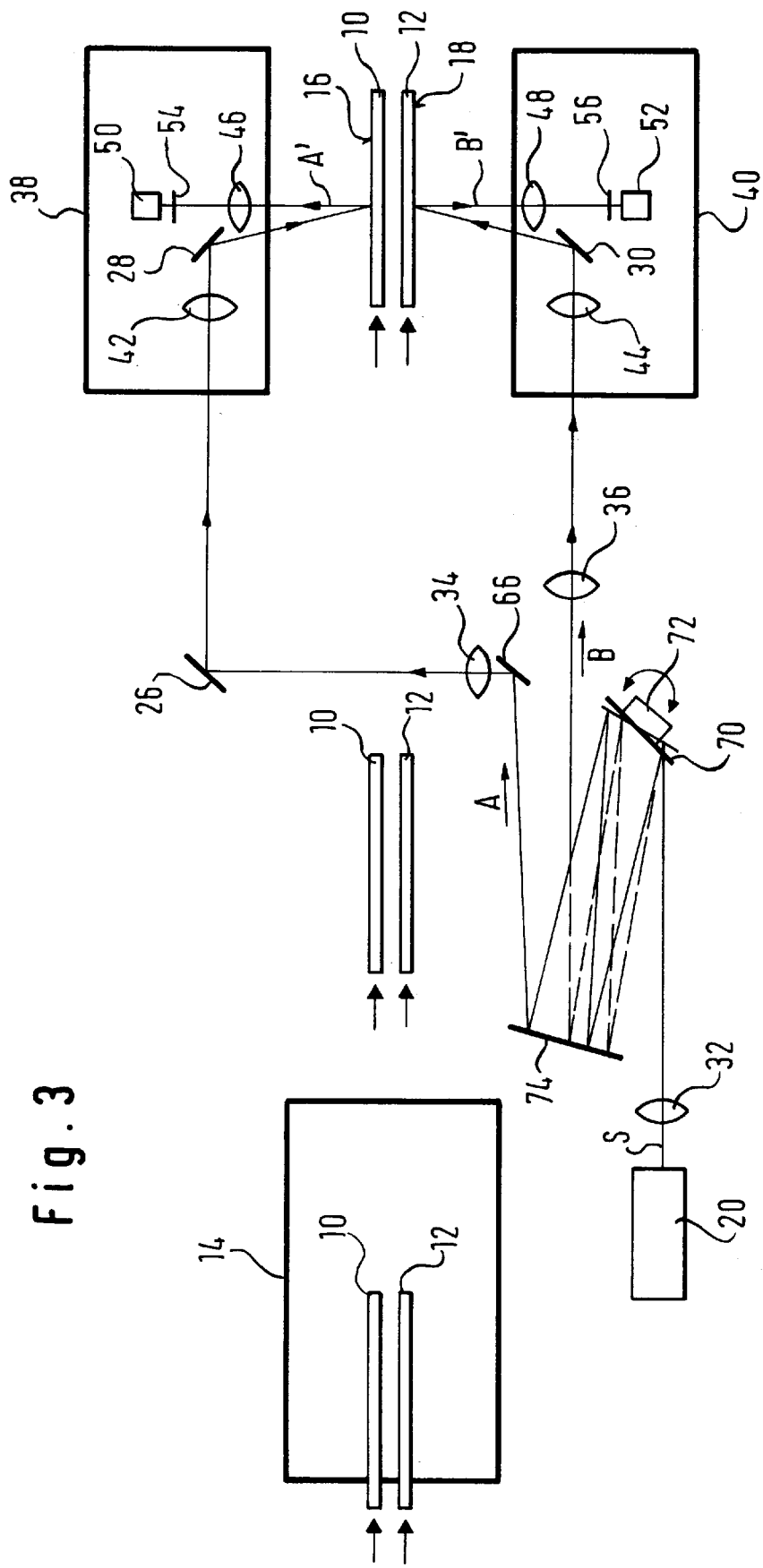
FIG. 3 is a diagrammatic presentation of a third embodiment of the invention.

Another embodiment of the invention is illustrated in FIG. 3. It is similar to one shown in FIG. 2, but the pivotable mirror 70 here is adjusted by means of a piezo element drive 72.

This has the advantage that very quick and precise positioning is made possible by piezo elements so that modulating frequencies up to several hundred Hertz are obtainable at duty cycles of almost 50%. The comparatively small angular deflection obtainable by piezo elements can be made sufficiently great by letting the excitation beam S impinge upon a plurality of mirrors in succession. These mirrors are driven in synchronism by piezo elements, and the overall angular swing is multiplied by the number of mirrors.

As an alternative, to be gathered from FIG. 3, the excitation beam may be coupled in between a mirror 70 adapted to be pivoted by a piezo element and another mirror 74 which is either pivotable or stationary and then be reflected back and forth several times until it is coupled out. Also in this manner a multiple angular deflection can be achieved. FIG. 3 shows how the excitation beam S follows a continuous line when the mirror 70 is in a first position directing the excitation beam S into channel A and how it follows a discontinuous line when the mirror 70 is in a second position directing the excitation beam into channel B. Both excitation channels finally reach a respective measuring head 38 and 40, as explained in detail with reference to FIGS. 1 and 2.

The embodiment including the piezo elements is especially useful if laser radiation is to be applied for excitation purposes. Piezo elements are suitable for switching at particularly great speeds and equally great accuracy and, in combination with the use of laser radiation, they permit a testing apparatus to be designed with rather small dimensions.

Furthermore, it is advantageous to provide the collector lens 32 in this arrangement as well since it reduces the beam cross section in the range of the pivotable mirror 70 so that the movable mirror or mirrors 70, 74 again may be given small dimensions. Moreover, the geometric separation of the two channels is facilitated due to the focussing, even when the angular deflections are small. Once more, the collector lenses 34 and 36 serve for collimation and, if desired, widening of the beam.

All the embodiments, in addition, may comprise a beam splitter (not shown) in the measuring head 38 and/or 40 so that the intensity modulated excitation radiation may be directed at two or more different points of examination on the workpiece surface.

The features as defined in the present specification, figures, and claims may be essential to implementing the invention, both individually or in any desired combination.

What is claimed is:

1. A method for nondestructive testing of a workpiece, comprising:
    directing a continuous electromagnetic excitation beam (S) periodically in different directions to provide a plurality of intensity modulated beams (A and B) which are directed at different noninterfering points of examination on a workpiece surface (16, 18) to produce thermal radiation at said points of examination distinguishable from the incident electromagnetic excitation beam; and
    detecting said thermal radiation emitted by said points of examination for evaluation.

2. The method as claimed in claim 1, wherein the excitation beam (S) is deflected at a frequency in the range of from approximately 0.1 to 500 Hz.

3. The method as claimed in claim or 1, wherein the excitation beam (S) is directed in two directions (A, B) at a duty cycle of approximately 50% and modulated as two excitation beams (A, B) shifted in phase by approximately 180°.

4. The method as claimed in claim 1, wherein the excitation beam (S, A, B) is split up into a plurality of divisional beams.

5. The method as claimed in claim 1, wherein the thermal radiation from the workpiece is detected for measuring thickness of a layer of a coating on a workpiece.

6. An apparatus for nondestructive testing of a workpiece including an excitation source (20) to emit an electromagnetic excitation beam (S), the apparatus comprising:
    an optical means (22, 26; 60, 64, 66, 68, 26; 70, 74, 66, 26) to modulate the intensity of the excitation beam (S) and to direct the excitation beam at points of examination on a workpiece surface (16, 18), said optical means including
        modulating means (22; 60; 70) for periodically deflecting the excitation beam in different directions (A, B) and
        directional means (26; 64, 66, 68, 26; 74, 66, 26) for directing the excitation beam in each direction (A, B)

at different noninterfering points of examination on a workpiece surface (16, 18) to produce thermal radiation at said points of examination distinguishable from the incident electromagnetic excitation beam; and detector means (50, 52) to detect said thermal radiation emitted by said points of examination on a workpiece surface (16, 18).

7. The apparatus as claimed in claim 6, wherein the detector means comprises a plurality of detectors (50, 52) to detect the thermal radiation emitted by the different points of examination.

8. The apparatus as claimed in claim 6, wherein the modulating means comprise an adjustable mirror (22; 60; 70) adapted to direct the excitation beam (S) in the different directions (A, B).

9. The apparatus as claimed in claim 6, wherein the modulating means comprise a rotatable mirror (22) having an axis of rotation perpendicular to the mirror axis and recesses and further being disposed to transmit or reflect the excitation beam (S), depending on the rotary position of the rotatable mirror.

10. The apparatus as claimed in claim 9, wherein the mirror (22) is round and has segments cut out from its periphery at regular intervals.

11. The apparatus as claimed in claim 6, wherein the modulating means comprise a pivotable mirror (60; 70) having a pivot axis in parallel with the mirror plane and being disposed with respect to the excitation source (20) for transmitting or reflecting the excitation beam (S), depending on the pivot position of the pivotable mirror.

12. The apparatus as claimed in claim 6, wherein the modulating means comprise a pivotable mirror (60; 70) having a pivot axis in parallel with the mirror plane and being disposed with respect to the excitation source (20) for directing the excitation beam (S) in any one of a plurality of defined directions, depending on the pivot position of the pivotable mirror.

13. The apparatus as claimed in claim 12, wherein the modulating means comprise a plurality of mirrors (70, 74) which are arranged substantially opposite each other to direct the excitation beam (S) by multiple reflections in one of several defined directions (A, B).

14. The apparatus as claimed in claim 13, wherein at least one of the mirrors (70, 74) is adapted to be pivoted back and forth by means of a piezo element (72) between two defined angular positions.

15. The apparatus as claimed in claim 6, wherein the optical means comprises at least one beam splitter to split the excitation beam (S, A, B) into a plurality of divisional beams.

16. The apparatus as claimed in claim 6, comprising a collector lens (32) disposed between the excitation source (20) and the optical means (22; 60; 70) to focus the excitation beam (S).

17. The apparatus as claimed in claim 6, wherein the directional means comprise a lens assembly (34, 36) to collimate the intensity modulated excitation beam (S, A, B).

18. The apparatus as claimed in claim 6, wherein the detector means detects the thermal radiation for measuring thickness of a layer of a coating on a workpiece.

* * * * *